US009839493B2

United States Patent
Maneuf et al.

(10) Patent No.: US 9,839,493 B2
(45) Date of Patent: Dec. 12, 2017

(54) REINFORCEMENT STRUCTURE FOR CORONAL-RADICULAR DENTAL RECONSTITUTION, METHOD FOR PERFORMING CORONAL-RADICULAR DENTAL RECONSTITUTION, CORONAL-RADICULAR DENTAL RECONSTITUTION

(71) Applicants: Bernard Maneuf, Voiron (FR); André Collombin, Voiron (FR); Bruno Clunet-Coste, Saint Etienne de Crossey (FR)

(72) Inventors: Bernard Maneuf, Voiron (FR); André Collombin, Voiron (FR); Bruno Clunet-Coste, Saint Etienne de Crossey (FR)

( * ) Notice: Subject to any disclaimer, the term of this patent is extended or adjusted under 35 U.S.C. 154(b) by 0 days.

(21) Appl. No.: 14/694,117

(22) Filed: Apr. 23, 2015

(65) Prior Publication Data
US 2015/0305829 A1 Oct. 29, 2015

(30) Foreign Application Priority Data
Apr. 23, 2014 (FR) .................... 14 00956

(51) Int. Cl.
*A61C 5/00* (2017.01)
*A61C 13/30* (2006.01)
*A61C 5/35* (2017.01)

(52) U.S. Cl.
CPC ............. *A61C 5/005* (2013.01); *A61C 5/35* (2017.02); *A61C 13/30* (2013.01)

(58) Field of Classification Search
CPC .............................. A61C 5/005; A61C 13/30
USPC ................................... 433/225, 228.1
See application file for complete search history.

(56) References Cited

U.S. PATENT DOCUMENTS

| | | | |
|---|---|---|---|
| 4,936,776 A | 6/1990 | Kwiatkowski | |
| 5,915,970 A | 6/1999 | Sicurelli, Jr. et al. | |
| 6,183,253 B1 * | 2/2001 | Billet | A61C 13/30 433/224 |
| 6,197,410 B1 * | 3/2001 | Vallittu | A61K 6/0044 428/292.1 |
| 6,371,763 B1 * | 4/2002 | Sicurelli, Jr. | A61C 13/30 433/220 |
| 2011/0294095 A1 | 12/2011 | Jancar et al. | |

FOREIGN PATENT DOCUMENTS

| | | |
|---|---|---|
| CH | 562605 A5 | 6/1975 |
| DE | 3825601 A1 | 3/1989 |
| EP | 0432001 A1 | 6/1991 |
| FR | 2588181 A1 | 4/1987 |
| FR | 2669211 A2 | 5/1992 |

(Continued)

*Primary Examiner* — Pedro Philogene
*Assistant Examiner* — David C Comstock
(74) *Attorney, Agent, or Firm* — Oliff PLC

(57) ABSTRACT

A structured reinforcement for a coronal-radicular dental reconstitution comprising:
a plurality of pins having diameters ranging from 0.1 mm to 0.5 mm,
an assembly part configured to group the plurality of pins so as to form a bundle of pins, said assembly part partially covering the length of the pins so that each pin presents a free end mobile in flexion with respect to the other pins of the bundle of pins.

19 Claims, 5 Drawing Sheets

(56) References Cited

FOREIGN PATENT DOCUMENTS

| | | |
|---|---|---|
| FR | 2753365 A1 | 3/1998 |
| GB | 1255875 A | 12/1971 |
| WO | 99/45859 A1 | 9/1999 |

\* cited by examiner

REINFORCEMENT STRUCTURE FOR CORONAL-RADICULAR DENTAL RECONSTITUTION, METHOD FOR PERFORMING CORONAL-RADICULAR DENTAL RECONSTITUTION, CORONAL-RADICULAR DENTAL RECONSTITUTION

BACKGROUND OF THE INVENTION

The invention relates to a reinforcement structure for a coronal-radicular dental reconstitution, to a method for performing coronal-radicular reconstitution and to coronal-radicular reconstitution.

STATE OF THE ART

In dentistry, and in particular in endodontics, when performing coronal-radicular dental reconstitution, and in particular to reconstruct the coronal part of a tooth, the radicular part of the tooth is first of all shaped by reaming. Reaming is performed by means of cylindroconical rotary or ultrasonic tools.

After shaping, a post is generally inserted and sealed in the root canal to act as anchoring for a coronal reconstitution. To ensure a good mechanical strength, the post has to penetrate up to the apical third of the root.

The root canals are hermetically sealed with specific materials, such as for example cylindroconical cones made from gutta-percha, zinc/eugenol oxide pastes, or resins in the form of bi-component preparations.

The coronal part of the coronal-radicular dental reconstitution is then arranged around the root post. Generally, the coronal part of the reconstitution is composed of composite resin.

This is the traditional pattern of "the pivot tooth": the tooth is constructed around the main root post which performs securing of the latter.

As described in Patent CH-A-562605, the posts can be made from metallic material and are each provided with a thread designed to screw the base of the post into the root canal. These posts are manufactured by turning and their cross-section is always circular with a cone-shaped or cylindroconical profile, with re-entrant or external angles.

Posts made from prefabricated composite material, which may be reinforced by fibers, are described in the documents FR 2588181, U.S. Pat. No. 4,936,776, DE-A-3825601 and EP-A-0432001.

The posts present a finite rectilinear cylindrical or cylindroconical shape and a rigid structure.

However, the canal is often of irregular shape, for example of flattened, oval or figure-of-eight cross-section. It may be very tapered in its coronal part and of ovalar cross-section. The canal can be curved and badly centred and the roots can be flat or concave.

To fit the post in the root canal, the dental practitioner therefore has to enlarge the canal and rectify its path. Fitting of posts can therefore be dangerous. Indeed, preparation of the housing of the post, by mechanical enlargement, requires circular preparations with displacement of the canal on the side of the curve, weakening of the canal wall and a high risk of fragilization and perforation.

In addition, seeking to make a maximum of contacts between the post and the canal walls, while at the same time trying to limit dentinal mutilation, lead the practitioner to make the following choice:

either using drills of large diameter with a large risk of perforation, or using a drill of reasonable diameter; but in this case the post will only have partial contacts with the areas that are not instrumented, or blemished by sealing material, which leads to poor adhesion and poor transmission of stresses.

The document FR-A-2753365 describes an endocanalar post. The post is formed by a core coated with sleeves. The core made from composite material is semi-rigid and flexible: it is composed of an organic matrix reinforced by fibers. The sleeves are made from composite material pre-impregnated with resin, and are in a pasty state prior to polymerization.

Before and during its insertion into the root canal, the inlay, of cylindrical cross-section, is therefore flexible and malleable. The material is then polymerized as required by cross-linking means to change to a second polymerized state.

This type of reinforcement enables the canal to be less enlarged, reducing the risks of fragilization or of perforation of the canal walls.

However the state prior to polymerization of the resin impregnating the reinforcement and the extreme malleability of the post make insertion of the latter in a tooth canal and complete photo-polymerization at the level of the apex extremely random.

It has been observed that the pulp chamber of a lower molar in certain cases has the shape of a rectangular parallelepiped. The whole of the mesial roots are curved and have a concaveness of the distal wall, and 99% present a concaveness of the mesial wall. The upper premolars have a mesial concaveness and frail roots. The canal is of oval cross-section or even in the shape of a "figure-of-eight" in its first coronal third. The only rectilinear part of the canal is in general located in the coronal third of the root, and the canal is tapered with a flattened cross-section.

Rectification of the canal to make it rectilinear weakens the strength of the anchoring.

The document GB 1255875 describes a pivot adaptable, case by case, to the morphology of the root of the tooth. The anatomical tooth canal anchoring has a non-circular cross-section, in particular in the form of an ellipse or a bean. This shape enables the contact areas between the dental post and the root canal to be increased and gives a better distribution of the mechanical forces.

The coronal part of a coronal-radicular dental reconstitution can also be strengthened by inserting auxiliary mini-posts (Fibercone® product from RTD) laterally to the main post. These posts correspond to the traditional layout of the central post of the pivot tooth. The accessory posts do not strengthen the whole of the coronal part of a coronal-radicular reconstitution.

OBJECT OF THE INVENTION

The object of the invention is to remedy the shortcomings of the prior art and in particular to propose a structural reinforcement for coronal-radicular dental reconstitution reinforcing both the coronal part and the radicular part in continuity while at the same time preventing risks of weakening or perforation of the canal walls.

This object tends to be achieved by the appended claims.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF A PREFERRED EMBODIMENT OF THE INVENTION

Figure 1:
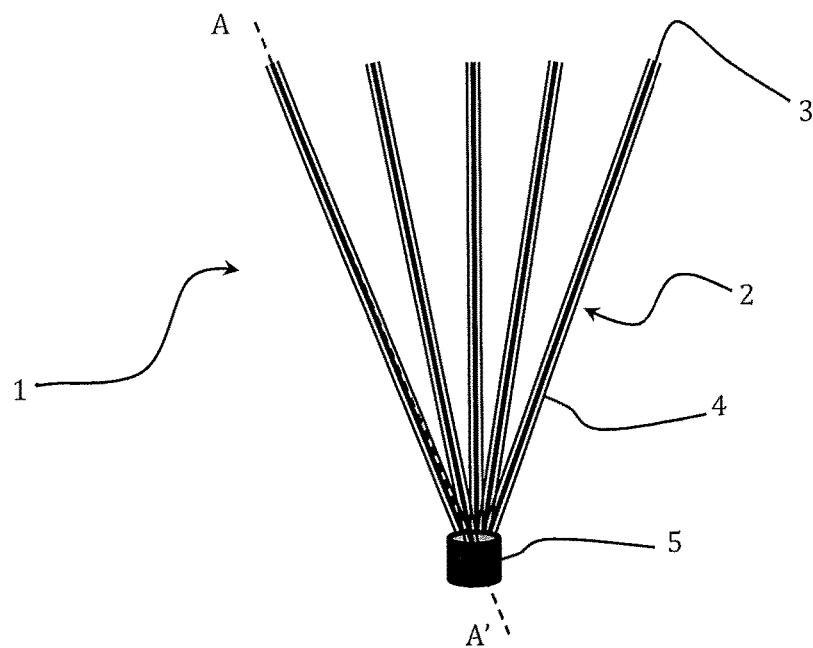
FIGS. 1 and 2 represent reinforcement structures for coronal-radicular dental reconstitution according to two embodiments, in schematic manner, in cross-section.

As illustrated in FIG. 1, the reinforcement structure 1 for a coronal-radicular dental reconstitution comprises a bundle of pins 2.

What is meant by bundle of pins is a set of longilinear elements linked to one another in the lengthwise direction.

The bundle comprises at least two pins 2. Preferentially, the bundle comprises from 2 to 10 pins, and, even more preferentially, from 3 to 10 pins and, even more preferentially, from 3 to 5 pins.

The number of pins is advantageously inversely proportional to the diameter of the pins.

Pins 2 are advantageously of identical length. They thus form a bundle of homogeneous shape.

Figure 2:
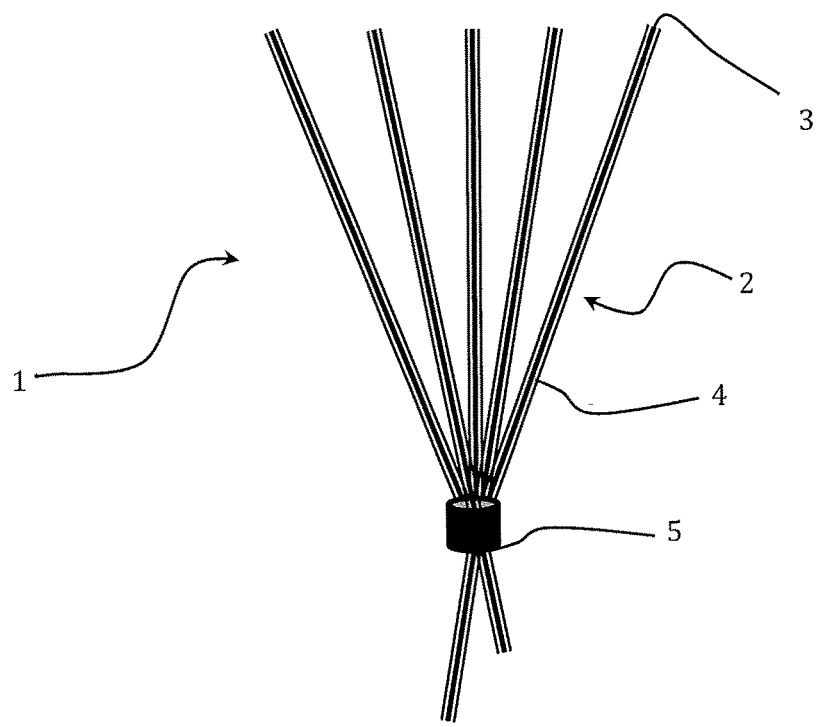

As represented in FIG. 2, pins 2 can have different lengths, their ends being offset.

Pins 2 are advantageously flexible so as to be able to be easily inserted in the tooth canal and to adapt to the complex morphology of the tooth canals.

What is meant by flexible is a supple element that can bend easily.

In FIG. 1, pins 2 are straight: they are represented in schematic manner. In reality, as they are flexible, they can present a curved shape.

Pins 2 have a small diameter. What is meant by small diameter is a diameter less than or equal to 1 mm, and preferentially less than or equal to 0.8 mm. Even more preferentially it is less than or equal to 0.5 mm.

Preferentially, the diameter of pins 2 is comprised between 0.1 mm and 0.8 mm, and, even more preferentially, it is comprised between 0.1 mm and 0.5 mm.

Pins 2 can thus be adapted to numerous canal structures, even to very confined structures.

According to one embodiment, pins 2 have an identical diameter, i.e. all the pins have about the same diameter to within 0.05 mm.

According to another embodiment, pins 2 have an increasing cross-section from the centre of the bundle to the periphery of the bundle.

For example, the pin in the central position of the bundle can have a diameter of 0.8 mm and the pins in peripheral position can have a diameter of 0.3 mm.

According to another example, the bundle can be formed by two pins with a diameter of 0.5 mm, two pins with a diameter of 0.3 mm and two pins with a diameter of 0.15 mm.

The whole of the coronal part is advantageously reinforced.

The diameter of the pin can also vary all along its length and the pin can have a cylindroconical, staged cylindrical, or double-conicity geometry or a geometry with a variable conicity over its whole length.

According to another embodiment, pins 2 can have a decreasing cross-section from the centre of the bundle to the periphery of the bundle.

Pins 2 are made from composite material: pins 2 are formed by at least one fiber 3 coated by a polymer matrix 4.

Advantageously, the polymer matrix will be chosen by the person skilled in the art. It has to enable the fibers to be solidly associated to the other to form a strong fibered composite pin.

Preferentially, each pin 2 comprises several fibers 3 independent from one another or in the form of an assembly of fibers, the fibers being for example able to be twisted and possibly flocked, covered by a coating.

The fibers are preferably unidirectional long fibers. Fibers 3 of the same pin 2 are coated in a polymer matrix 4.

Each pin 2 is formed by fibers 3 coated in a polymer matrix 4.

Pins 2 are preferably, individually, completely polymerized so as to form flexible pins 2 independent from one another.

Fibers 3 act as reinforcement within pins 2, along their large axis (axis AA' of FIG. 1).

Fibers 3 of pins 2 can be of identical or different nature in any one pin 2.

Fibers 3 can be of identical or different nature from one pin 2 to the other.

Any sort of fiber can be used provided it has a coating compatible with the assembly resin used. They can be artificial manufactured fibers, such as siliceous fibers, carbon fibers, or organic fibers (of poly(p-phenyleneterephtalamide) (PPD-T), aramid, nylon, etc type) or even natural fibers.

As represented in FIGS. 1 and 2, pins 2 are assembled, mechanically connected by an assembly part 5. All the pins 2 are secured to one another by assembly part 5. Assembly part 5 is configured to group the plurality of pins 2. Assembly part 5 partially covers the length of pins 2 and is configured to mechanically hold the pins together and to leave a part of the length of pins 2 free. Each pin presents a free end mobile in flexion with respect to the other pins of the bundle of pins. Advantageously, each pin presents a free end mobile in flexion and in translation with respect to the other pins of the bundle of pins. The pins can also slide freely with respect to one another along their large axis, while being curbed by their reciprocal friction.

Each pin advantageously presents a mobility in the three dimensions of space.

Assembly part 5 is arranged so that at least a half of the length of pins 2 is not secured by assembly part 5.

Assembly part 5 is for example positioned in the first third of the length of the bundle of pins 2 so as to allow flexion and axial sliding of one pin with respect to the other.

Preferentially, assembly part 5 is arranged at one of the ends of the bundle of pins 2 to hamper at the minimum the freedom of flexion of pins 2 relatively with respect to one another.

What is meant by end is that assembly part 5 is positioned on the first quarter of the length of the pin.

Pins 2 are secured on one side only so as to form a tapered bundle. What is meant by tapered bundle is a bundle of pins having the form of a bouquet, i.e. the cross-section of the bundle of pins 2 at the level of the assembly part is strictly smaller than the cross-section of the bundle of pins at the level of the free end, i.e. the end opposite assembly part 5.

However the pins can be assembled in circular or oval manner or so as to have a flat cross-section, according to the shape that will be given by assembly part 5.

The pins can be secured at their end but the ends may not coincide, for example in the case of pins 2 of different lengths.

Even more preferentially, assembly part 5 is positioned on the end of the pins, the extreme edge of the pins, i.e. the pins are only salient on one side of assembly part 5.

Preferentially, assembly part 5 is made from composite resin.

The resin is chosen from methacrylate, polyetheretherketone and epoxide resins.

The resin can contain additives in the form of mineral or organic colorants, as well as micronic or nanometric particles designed to modify its consistency or its mechanical performances.

For example pins 2 are secured by a sleeve made from polymerized composite resin. What is meant by sleeve is a cylindrical part open at least at one of its two ends.

Assembly part 5 can be simply achieved by sticking the ends of the pins with a composite glue. This technique is preferentially chosen when the ends of the pins are offset.

The ends of the pins are offset, in assembly part 5, when a thin, pointed apex is sought to be achieved for the bundle of pins.

Assembly part 5 is configured so as to keep pins 2 together when they are handled. It is also configured in such a way that it is possible to remove pins 2 one by one or in a small quantity in the case where the structure receiving the bundle of pins is of smaller dimension than the bundle of pins.

When one or more pins are removed, the assembly part continues to maintain the remaining fibers. The energy required to tear a pin off from the bundle is smaller than the energy required to open, or break, assembly part 5.

The size of the bundle of pins 2 is adaptable according to requirements.

In a preferential embodiment of the invention, assembly part 5 does not prevent pins 2 from sliding with respect to one another over at least one tenth of their length and it blocks them or retains them when this distance is exceeded. For example, the pins can slide with respect to one another along their large axis (axis AA' of FIG. 1). Pins 2 can cross one another within the structure.

Advantageously, assembly part 5 does not prevent pins 2, also called micro-posts, from moving with respect to one another in the three dimensions.

Figure 3:
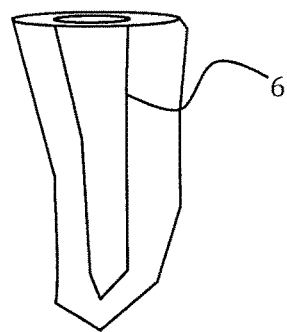
FIGS. 3 to 6 represent different steps of a method for performing a coronal-radicular reconstitution, according to one embodiment, in schematic manner, in cross-section.
Figure 4:
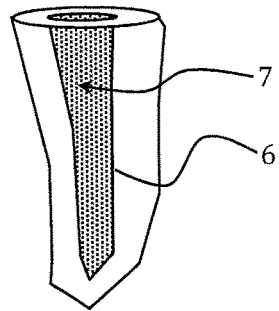
Figure 5:
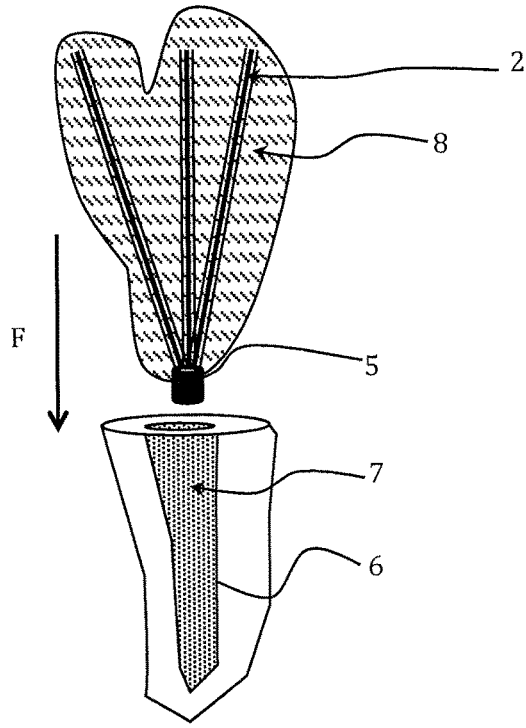

As represented in FIGS. 3 to 5, the method for performing a coronal-radicular dental reconstitution 9, for example on a laboratory model, for example a mould, comprises the following successive steps:
1) at least partially filling a tooth canal 6 of the laboratory model with a first composite resin 7,
2) providing reinforcement structure 1 described above, impregnated with a second composite resin 8,
3) inserting reinforcement structure 1 in tooth canal 6,
4) polymerizing the composite resins 7, 8 so as to obtain a coronal-radicular reconstitution 9.

FIG. 3 represents a root canal 6. In this case it is a cavity. The method can be performed on any laboratory model presenting a cavity.

During step 1), root canal 6, or the cavity, is filled with a first composite resin 7 (FIG. 4). Preferentially, it is completely filled with resin.

Reinforcement structure 1 is impregnated with a second composite resin 8 (step 2). Preferentially, reinforcement structure 1 is impregnated up to saturation, i.e. at least pins 2 of reinforcement structure 1 are completely covered by first composite resin 8 (FIG. 5).

Preferentially, first composite resin 7 and second composite resin 8 are identical, i.e. they are of the same nature, the same resin is involved. Even more preferentially, first composite resin 7 and second composite resin 8 are one and the same bonding resin. This enables better mechanical securing to be achieved.

The resins are polymerizable.

Advantageously, the same composite glue is used for making the coronal part, the coronal-radicular part and the apical part of the coronal-radicular dental reconstitution.

According to another embodiment, second composite resin 8 independently covering each pin 2 can be different from first composite resin 7.

During step 3, reinforcement structure 1, impregnated with second composite resin 8, is inserted in tooth canal 6 (arrow F of FIG. 5).

Figure 6:
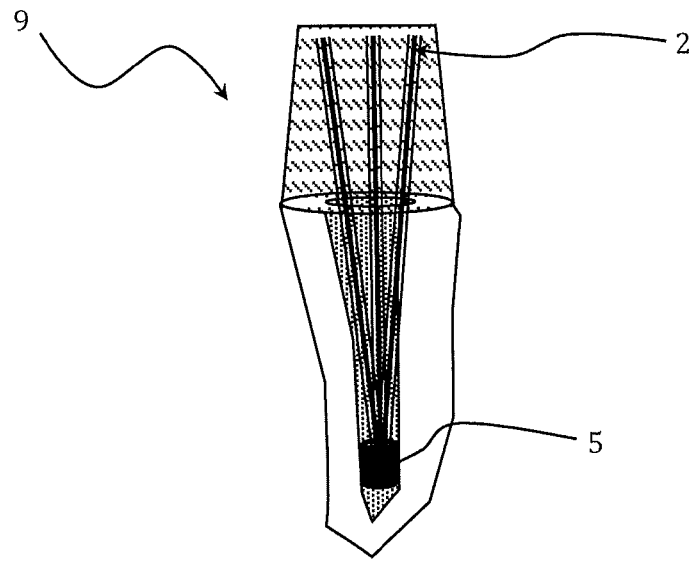

Preferentially, all the pins 2 of reinforcement structure 1 are held secure by assembly part 5. Assembly part 5 is positioned in the apical part of the structure so as to be in contact with the enlargement made with the preparation drill (FIG. 6).

Assembly part 5 advantageously presents the same geometry as the apex of the enlargement drill used for preparation of tooth canal 6. Assembly part 5 thus fits perfectly in tooth canal 6.

Precise adjustment of the post improves both securing and sticking and also alleviates functional constraints.

Assembly part 5 and the bundle of pins 2, coated with resin, in intimate contact with the walls of the tooth canal, form a mechanically compact and coherent assembly, thus achieving a continuity of volume, participating in distribution of the stresses without breaking of the load and without presenting stress concentration areas which may give rise to breakage.

Pins 2 of reinforcement structure 1 are dispersed in continuity in the whole of first reconstitution composite resin 7. Reinforcement structure 1 fits into the geometry of the cavity by sliding of pins 2 with respect to one another.

During step 4, first composite resin 7 and second composite resin 8 are polymerized. After polymerization, pins 2 are frozen in coronal-radicular reconstitution 9.

Polymerization enables a coronal-radicular dental reconstitution 9 to be made ensuring its rigidity by its own shape and the architecture of its strengtheners.

The coronal part is advantageously formed by the same pins 2 as the radicular part.

The coronal-radicular dental reconstitution 9 obtained according to the method is performed without performing rectification of tooth canal 6 in its corono-radicular part, up to $2/3$ of the coronal part. The canal can be instrumented with enlargement drill bits of variable conicity to perform the endodontic treatment. At the apex, the conicity is therefore defined by this instrumentalization.

Furthermore, it has the same geometry as the apex of the enlargement drill used when preparation of tooth canal 6 for the endodontic treatment is performed and adjusts easily to the anatomic particularities of the pulp chambers and of the tooth canals.

Figure 7:
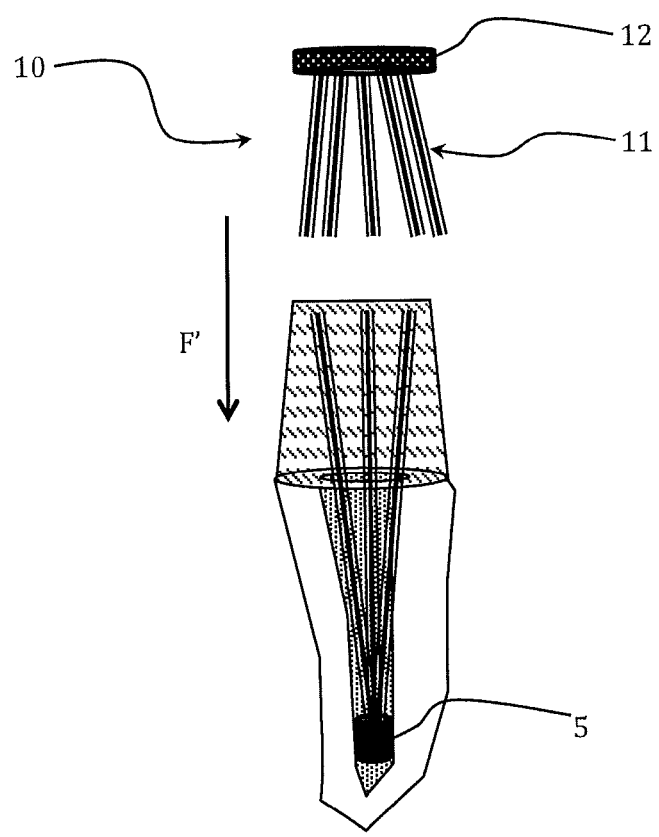
FIGS. 7 and 8 represent different steps of a method for performing a coronal-radicular reconstitution, according to another embodiment, in schematic manner, in cross-section, FIG. 9 represent two reinforcement structures in a tooth canal, in schematic manner, in cross-section.
Figure 8:
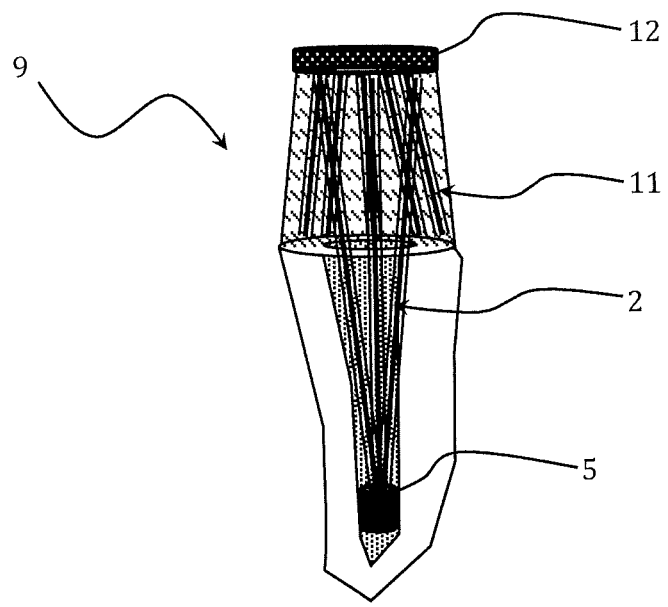

Before the polymerization step, and as represented in FIGS. 6 to 8, a second structure 10 can be deposited on first reinforcement structure 1, pins 11 of second reinforcement structure 10 intermeshing with pins 2 of first reinforcement structure 1 by sliding. Second reinforcement structure 10 is inserted capping first structure 1 (arrow F' of FIG. 7). Second reinforcement structure 10 fits onto first structure 1 by sliding against radicular pins 2 to form a pluridimensional fiber lattice.

Second reinforcement structure 10 is also formed by a bundle of pins 11 made from composite material: long fibers elongate in the large axis of each pin are covered by an entirely polymerized polymer. Pins 11 are independent from one another. Pins 11 of second reinforcement structure 10 are secured by an assembly part 12.

Pins 11 of second reinforcement structure 10 can also be covered by a polymerizable composite resin before being inserted capping first reinforcement structure 1. Preferentially, the composite resin is the same as that covering pins 2 of first structure 1.

According to another embodiment, pins 2 of first reinforcement structure 1 present a sufficient quantity of composite resin and there is no need to add resin on pins 11 of second reinforcement structure 10 (case of the schematic representation of FIG. 7).

An array of intermeshed pins 2, 11 is obtained (FIG. 8). The mechanical stresses are better distributed and the structure is more solid.

The coronal-radicular dental reconstitution 9 obtained by the method comprises at least one reinforcement structure 1, reinforcement structure 1 being sunk in at least one polymerized composite resin.

More particularly, the structure made from composite material reinforced with fibers for coronal-radicular dental reconstitution comprises a bundle of pins independent from one another. A portion of the pins is secured by an assembly part.

The reinforcement structure and the resin form a self-supporting structure ensuring the rigidity of the reconstitution.

According to another embodiment, the dental reconstitution comprises two reinforcement structures 1, 10, arranged one above the other, pins 2, 11 of the two structures being intermeshed. The additional reinforcement structure 10, the coronal reinforcement structure, forms a complement to the first radicular reinforcement structure 1.

Figure 9:
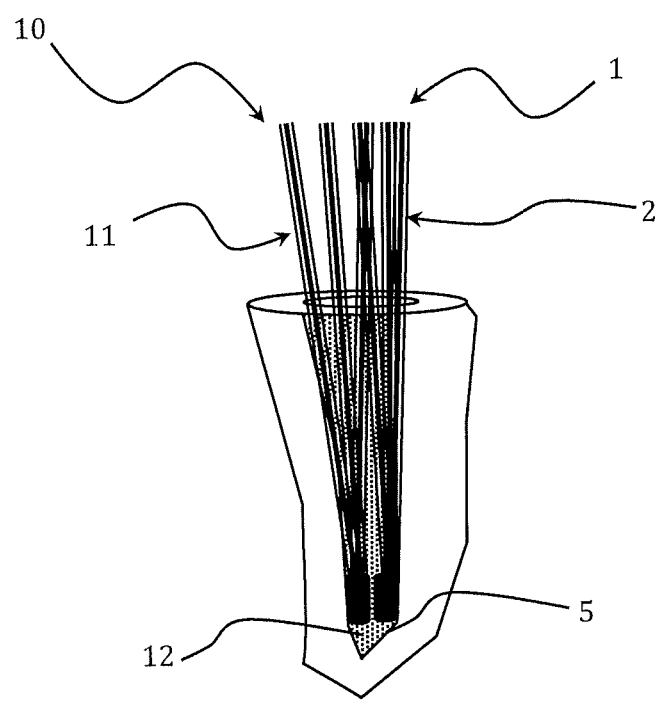

According to another embodiment, the dental reconstitution can also comprise reinforcement structures 1, 10 inserted side by side in the same tooth canal 6 (FIG. 9). The two reinforcement structures 1, 10 are inserted in the same tooth canal to form a single coronal-radicular dental reconstitution. Assembly parts 5, 12 of each reinforcement structure 1, 10 are arranged side by side in the canal and pins 2, 11 of the reinforcement structures intermesh with one another. The number of pins and/or the diameter of the pins is adjusted according to the shape and size of the cavity design to receive the reinforcement structure. Pins 2, 11 of each structure are independent from one another and adjust by flexion to the natural morphology of a tooth canal without enlargement to a defined shape.

According to a preferred embodiment, assembly part 5 is a heat-shrink sleeve. What is meant by heat-shrink is a part having the property of retracting under the action of heat. What is meant by sleeve is a case, an envelope able to adapt to the shape and dimension of the bundle of pins.

Figure 10:
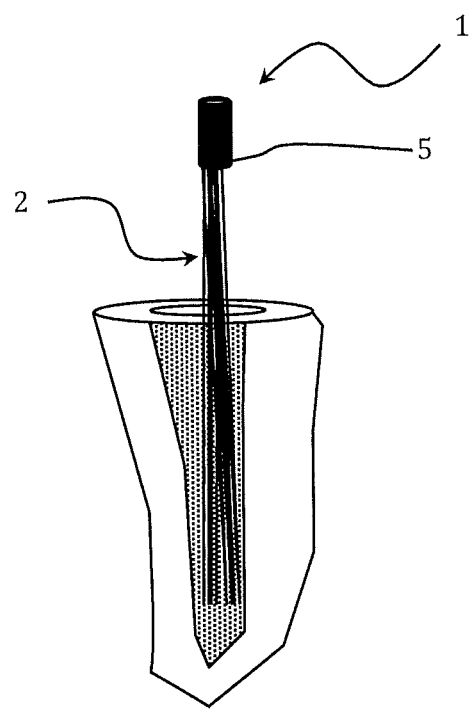
FIGS. 10 and 11 represent reinforcement structures in a tooth canal according to another embodiment of the invention, in schematic manner, in cross-section.
Figure 11:
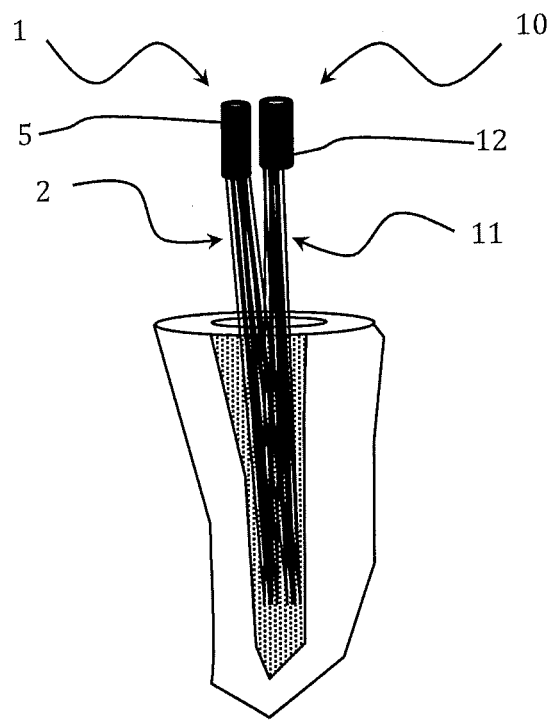

Preferentially, and as represented in FIGS. 10 and 11, in step 3) of the method for performing coronal-radicular dental reconstitution described above, reinforcement structures 1, 10, provided with heat-shrink sleeve, are inserted in the canal: pins 2, 11 are located at the level of the radicular part of the canal and assembly part 5, 12 is positioned above the coronal part. The assembly part is in distal position with respect to the apical part of the tooth canal.

Assembly part 5 advantageously acts as grip.

Before the polymerization step (step 4 of the method described above), a second reinforcement structure 10 can be deposited next to first reinforcement structure 1, in tooth canal 6 (FIG. 11).

In this configuration (assembly part located opposite the apical part of tooth canal), assembly part 5, 12 is eliminated at the end of the method for performing coronal-radicular dental reconstitution.

According to other variants, this positioning of the reinforcement structures can be performed with a bundle of pins provided with an assembly part of another nature. This part can be a simple sleeve, a casing, or any part enabling the pins to be kept together in the form of a bundle. The assembly part can initiate any shape on the bundle of pins, flattened in the same plane, ovoid, circular, triangular etc. There is no limit to the possible shapes.

The number of reinforcement structures 1, 10 inserted in the tooth canal depends on the size of said canal. FIG. 10 represents for example a canal in which a single reinforcement structure is inserted. FIG. 11 represents a canal in which two reinforcement structures are inserted side by side.

From 1 to 10 reinforcement structures can thus be inserted in the tooth canal.

The coronal-radicular reconstitution can for example be performed on laboratory dental models.

The coronal-radicular dental reconstitution snugly follows and respects the anatomical and physiological particularities of the root canal.

The reinforcement structure or structures extend in the whole volume of the radicular part and of the supra-gingival coronal part of the coronal-radicular dental reconstitution. They enable the whole of the material of the reconstitution constituting the coronal part and also the radicular part to be strengthened in continuity.

The invention claimed is:

1. A reinforcement structure for coronal-radicular dental reconstitution comprising:
    a plurality of pins having diameters ranging from 0.1 mm to 0.5 mm, and
    an assembly part configured to group the plurality of pins so as to form a bundle of pins, said assembly part partially covering a length of the plurality of pins so that each pin presents a free end mobile in flexion with respect to the other pins of the bundle of pins,
    wherein each pin can slide freely along its large axis relative to the other pins.

2. The reinforcement structure according to claim 1, wherein the assembly part is arranged at one of the ends of the bundle of pins.

3. The reinforcement structure according to claim 1, wherein each pin is formed by fibers coated in a polymer matrix.

4. The reinforcement structure according to claim 3, wherein the fibers of the pins are of identical nature, in any one pin or from one pin to another pin.

5. The reinforcement structure according to claim 3, wherein the fibers of the pins are of different natures, in any one pin or from one pin to another pin.

6. The reinforcement structure according to claim 1, wherein the assembly part is made from composite resin.

7. The reinforcement structure according to claim 1, wherein the plurality of pins have the same diameter.

8. The reinforcement structure according to claim 1, wherein the plurality of pins have an increasing diameter from a centre of the bundle of pins to a periphery of the bundle of pins.

9. The reinforcement structure according to claim 1, wherein the plurality of pins have a decreasing diameter from a centre of a bundle of pins to a periphery of the bundle of pins.

10. The reinforcement structure according to claim 1, wherein the bundle of pins comprises from 3 to 10 pins.

11. The reinforcement structure according to claim 1, wherein at least half of the length of the pins is not covered by the assembly part.

12. The reinforcement structure according to claim 1, wherein one third or less of the length of the pins is covered by the assembly part.

13. The reinforcement structure according to claim 1, wherein the bundle of pins includes at least two pins of different lengths.

14. The reinforcement structure according to claim 1, wherein the assembly element is in a shape of a circle or an oval.

15. A method for performing a coronal-radicular dental reconstitution, comprising the following successive steps:

at least partially filling a tooth canal with a first composite resin, providing the reinforcement structure, according to claim 1, impregnated with a second composite resin, inserting the reinforcement structure impregnated with the second composite resin in the tooth canal, polymerizing the first composite resin and the second composite resin so as to obtain a coronal-radicular reconstitution.

16. The method according to claim 15, wherein the first composite resin and the second composite resin are identical.

17. The method according to claim 15, wherein, before the polymerization step, a second reinforcement structure is deposited on the first reinforcement structure, pins of the second reinforcement structure intermeshing with the pins of the first reinforcement structure by sliding.

18. The method according to claim 15, wherein, before the polymerization step, a second reinforcement structure is deposited next to the first reinforcement structure, in the tooth canal.

19. A coronal-radicular dental reconstitution obtained by the method according to claim 15.

* * * * *